US011013282B2

(12) United States Patent
Milescu et al.

(10) Patent No.: US 11,013,282 B2
(45) Date of Patent: May 25, 2021

(54) CUT-CHANGING CLOTHING BASED ON ADJUSTABLE STITCHING

(71) Applicant: Intel Corporation, Santa Clara, CA (US)

(72) Inventors: George Milescu, Bucharest (RO); Florin Papa, Bucharest (RO); Doru Gucea, Bragadiru (RO)

(73) Assignee: Intel Corporation, Santa Clara, CA (US)

( * ) Notice: Subject to any disclaimer, the term of this patent is extended or adjusted under 35 U.S.C. 154(b) by 524 days.

(21) Appl. No.: 15/576,574

(22) PCT Filed: Jun. 26, 2015

(86) PCT No.: PCT/IB2015/001314
§ 371 (c)(1),
(2) Date: Nov. 22, 2017

(87) PCT Pub. No.: WO2016/207682
PCT Pub. Date: Dec. 29, 2016

(65) Prior Publication Data
US 2018/0160758 A1 Jun. 14, 2018

(51) Int. Cl.
*A41H 43/02* (2006.01)
*D04B 1/14* (2006.01)
(Continued)

(52) U.S. Cl.
CPC ............... *A41H 43/02* (2013.01); *D04B 1/14* (2013.01); *D04B 21/14* (2013.01); *D04C 1/02* (2013.01);
(Continued)

(58) Field of Classification Search
CPC ...... D03D 15/0055; D04B 1/14; H01F 13/00; D06F 89/02; A41D 2300/50
See application file for complete search history.

(56) References Cited

U.S. PATENT DOCUMENTS 3,126,924 A * 3/1964 Kirkpatrick ........ D03D 15/0027 139/425 R
4,457,723 A 7/1984 Tate
(Continued)

FOREIGN PATENT DOCUMENTS

CN 1252460 A 5/2000
CN 1835690 A 9/2006
(Continued)

OTHER PUBLICATIONS

International Preliminary Report on Patentability for International Patent Application No. PCT/IB2015/001314, dated Jan. 4, 2018, 13 pages.
(Continued)

*Primary Examiner* — Nathan E Durham
(74) *Attorney, Agent, or Firm* — Jordan IP Law, LLC

(57) ABSTRACT

Systems, apparatuses and methods may provide for a clothing article including a first fabric having a first set of threads coupled to one another, wherein each thread in the first set of threads includes a metal compound with electropermanent magnet properties. Additionally, a second fabric may be coupled to the first fabric, wherein the second fabric includes a second set of threads having the metal compound with electropermanent magnet properties. In one example, electrical current may be applied to one or more target threads, wherein the electrical current may initiate a slide of the first fabric across the second fabric and/or initiate creation of a fold among the target threads.

14 Claims, 6 Drawing Sheets

(51) Int. Cl.

| | |
|---|---|
| ***D04B 21/14*** | (2006.01) |
| ***D04C 1/02*** | (2006.01) |
| ***H01F 7/02*** | (2006.01) |
| ***D06F 89/02*** | (2006.01) |
| *H01F 13/00* | (2006.01) |

(52) U.S. Cl.

CPC ........... *D06F 89/02* (2013.01); *H01F 7/0226* (2013.01); *A41D 2300/50* (2013.01); *A41D 2500/10* (2013.01); *A41D 2500/20* (2013.01); *H01F 13/00* (2013.01)

(56) References Cited

U.S. PATENT DOCUMENTS 4,515,850 A * 5/1985 Ishino .................. H01F 1/0027 264/112
6,210,771 B1 * 4/2001 Post ......................... H05K 3/10 428/100
7,817,002 B2 * 10/2010 Fullerton .................. A45F 5/02 335/306
7,821,367 B2 * 10/2010 Fullerton .............. H01F 7/0215 335/306
8,701,578 B2 * 4/2014 Chung ................... A41D 1/005 112/439
2003/0059609 A1 * 3/2003 Rodgers ................. D02G 3/441 428/373
2008/0025648 A1 1/2008 Maeda et al.
2009/0273422 A1 11/2009 Fullerton
2012/0271571 A1 10/2012 Bulumulla et al.
2014/0062970 A1 3/2014 Pant et al.
2014/0084045 A1 * 3/2014 Yang ........................ A61N 1/16 228/175
2014/0180624 A1 * 6/2014 Nikonov .............. G05D 23/192 702/130

FOREIGN PATENT DOCUMENTS

CN 101884433 A 11/2010
CN 1019936730 A 3/2011
CN 102127837 A 7/2011
CN 104354379 A 2/2015
WO 8600577 A1 1/1986

OTHER PUBLICATIONS

Knaian, Ara; "Electropermanent Magnetic Connectors and Actuators: Devices and Their Application in Programmable Matter"; 2010; Massachusetts Institute of Technology; pp. 1-206.
Wikipedia,"Electropermanent magnet", downloaded from en.wikipedia.org/wiki/Electropermanent_magnet, May 31, 2015, 7 pages.
International Search Report for International Patent Application No. PCT/IB2015/001314, dated Jun. 6, 2016, 5 pages.
Office Action for Japanese Patent Application No. JP2017-555555, dated Mar. 26, 2019, 6 pages, including 3 pages of English translation.

* cited by examiner

FIG. 1
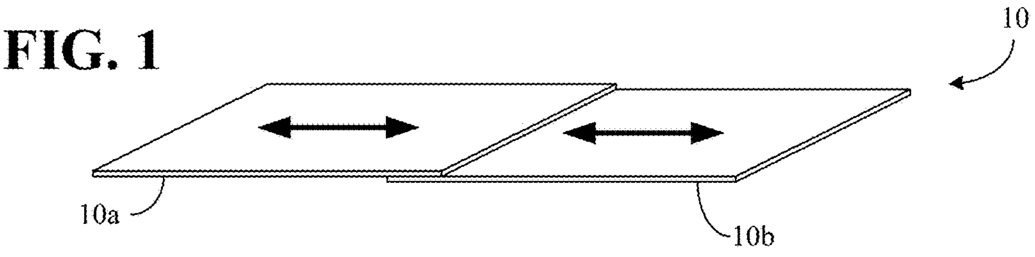
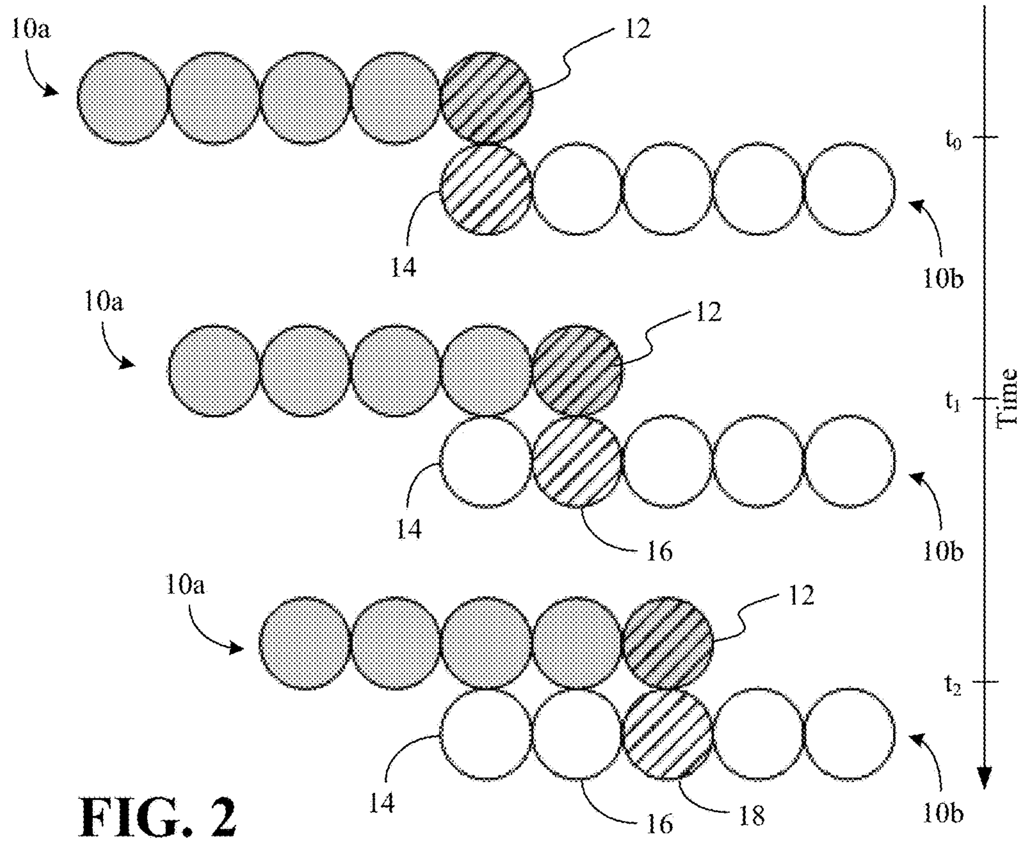
FIG. 2
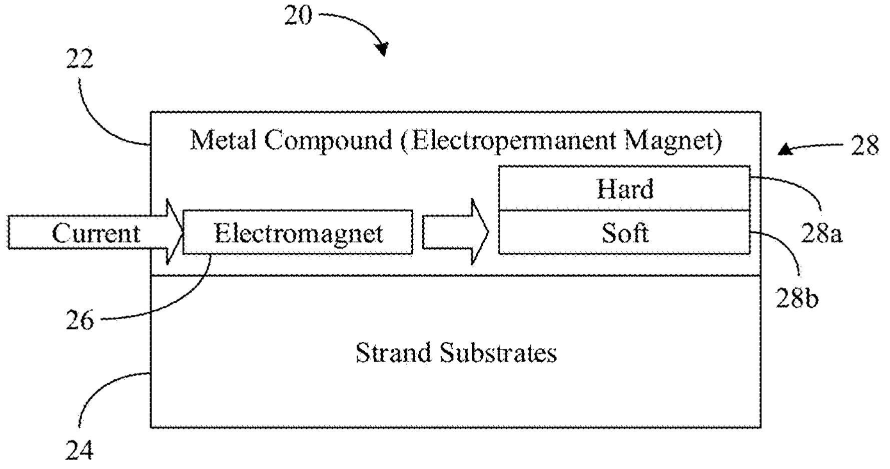
FIG. 3

FIG. 7A
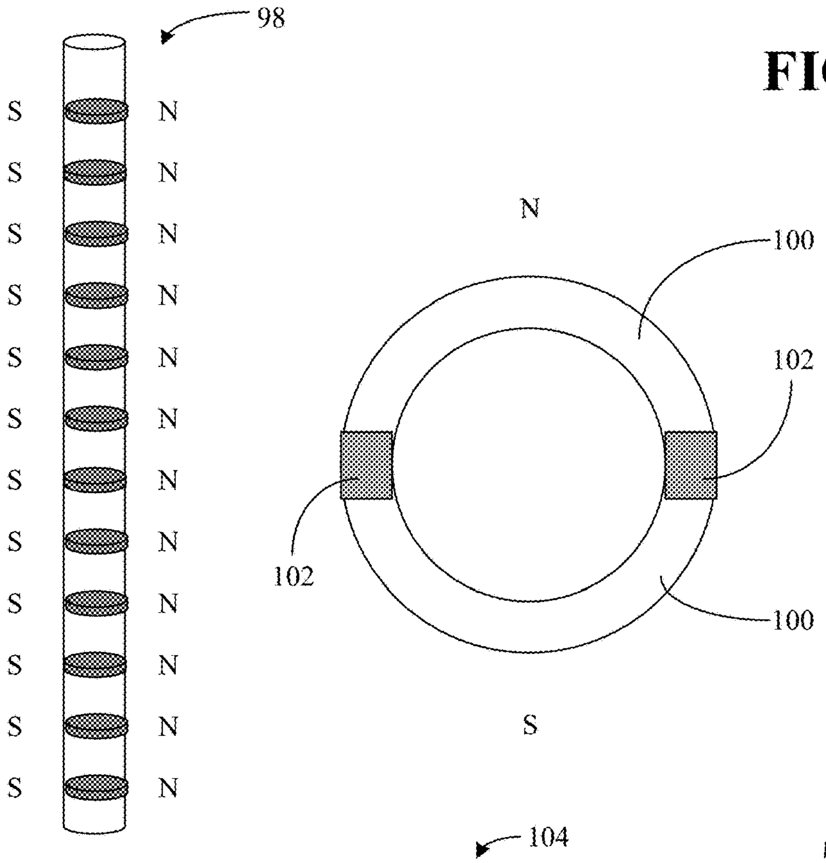
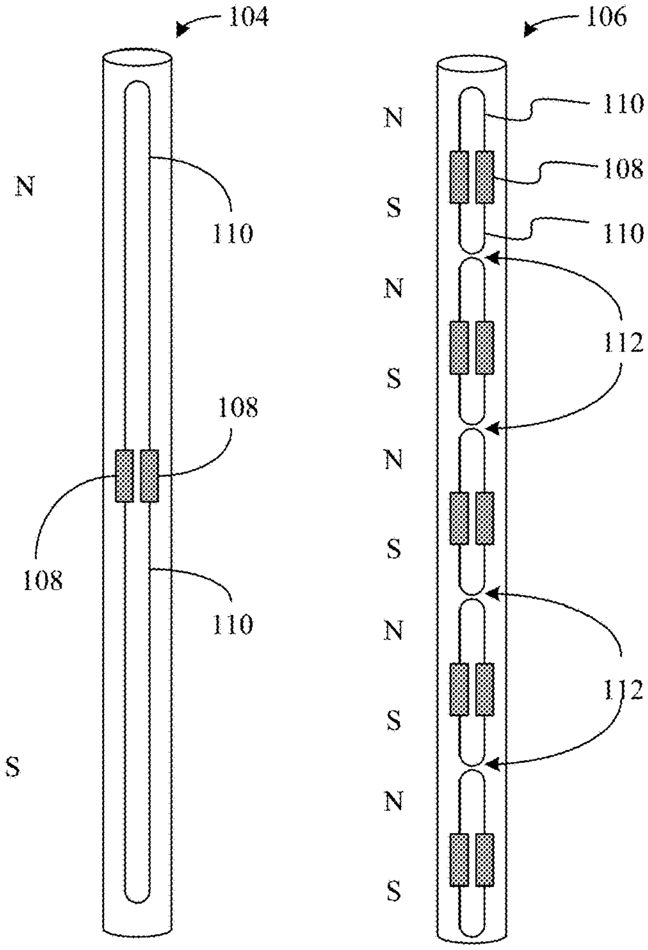
FIG. 7B

FIG. 9
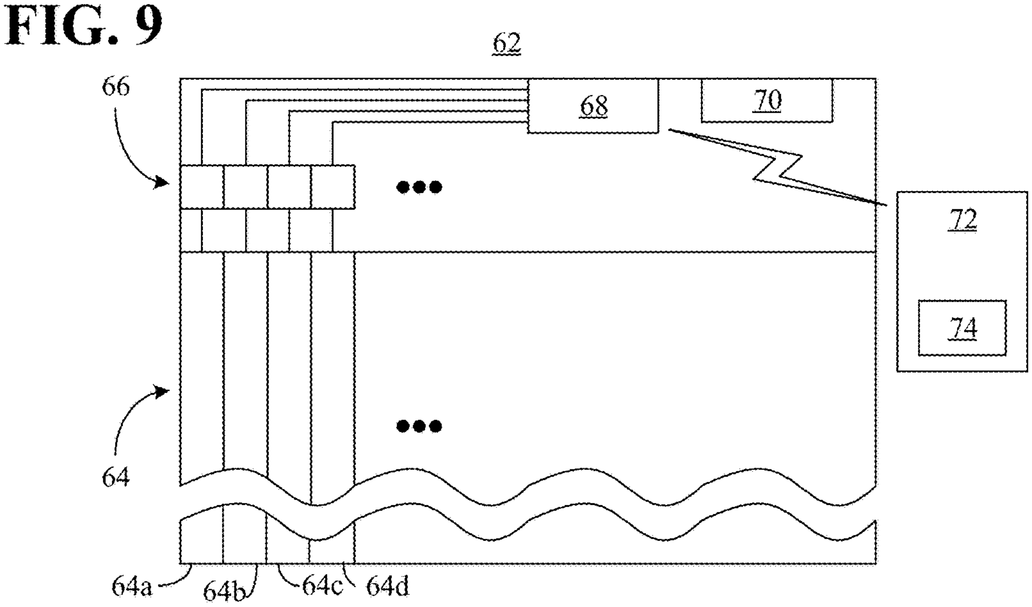
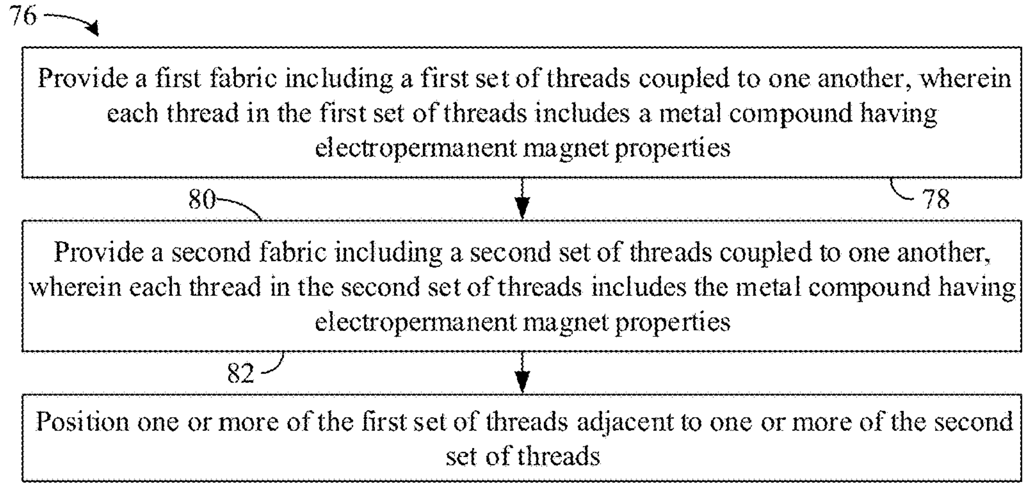
FIG. 10
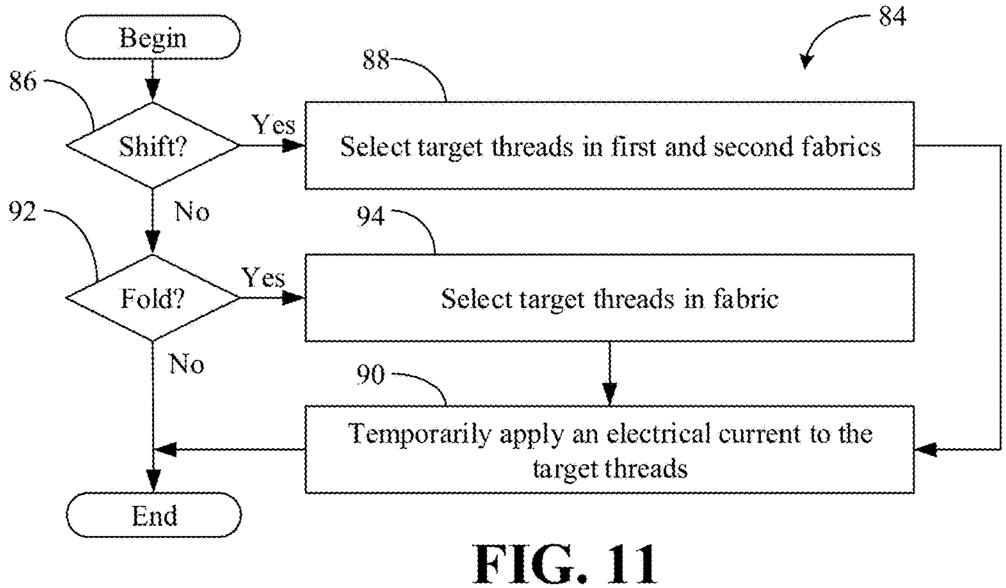
FIG. 11

CUT-CHANGING CLOTHING BASED ON ADJUSTABLE STITCHING

TECHNICAL FIELD

Embodiments generally relate to clothing. More particularly, embodiments relate to cut-changing clothing based on adjustable stitching.

BACKGROUND

Conventional clothing articles may be made of fixed-size pieces of fabric that are stitched together with thread. The sizes and shapes of the fabric pieces, together with the type of stitch may be selected by a fashion designer in order to determine the style and fit of clothing. Once an article of clothing is created, making adjustments may involve manually re-stitching (e.g., by a tailor) various portions of the clothing. Moreover, regardless of the changes made by a tailor, the overall cut of the clothing may remain the same.

BRIEF DESCRIPTION OF THE DRAWINGS

The various advantages of the embodiments will become apparent to one skilled in the art by reading the following specification and appended claims, and by referencing the following drawings, in which:

FIG. 1 is a perspective view of an example of a relative shift between a plurality of fabrics according to an embodiment;

FIG. 2 is an end view of an example of a relative shift between a plurality of fabrics according to an embodiment;

FIG. 3 is a block diagram of an example of thread model according to an embodiment;

FIG. 7A is an illustration of examples of magnetic distribution options for threads having laterally arranged electropermanent magnet properties according to embodiments;

FIG. 7B is an illustration of examples of magnetic distribution options for threads having longitudinally arranged electropermanent magnet properties according to embodiments;

FIG. 9 is a plan view of an example of a fabric according to an embodiment;

FIG. 10 is a flowchart of an example of a method of constructing a clothing article according to an embodiment; and FIG. 11 is a flowchart of an example of a method of operating a controller according to an embodiment.

DESCRIPTION OF EMBODIMENTS

Figure 4:
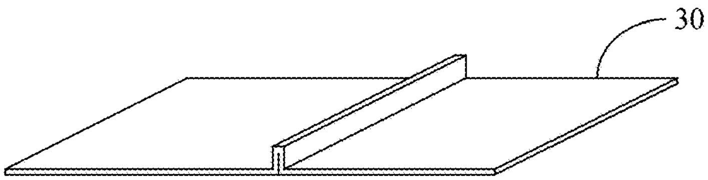
FIG. 4 is a perspective view of an example of a creation of a fold in a fabric according to an embodiment.

Turning now to FIGS. 1 and 2, a plurality of fabrics 10 (10*a*, 10*b*) is shown, wherein the fabrics 10 may generally be used, along with other fabrics (not shown), to construct an article of clothing such as, for example, formalwear (e.g., gowns, tuxedos), business clothing (e.g, suits, shirts, pants, blouses, skirts), active wear (e.g., exercise clothing, jerseys, headbands), underwear, military clothing (e.g., anti-gravity flight suits, camouflage), medical clothing (e.g., patient gowns, surgery masks), construction gear (e.g., toolbelts), and so forth. As will be discussed in greater detail, each of the fabrics 10 may include threads having one or more metal compounds with electropermanent magnet properties. Accordingly, when threads from a first fabric 10*a* are brought into proximity with threads of a second fabric 10*b*, a magnetic bond between the two fabrics 10 may be created (e.g., a magnetic "stitch"). In the illustrated example, the relative positioning between the fabrics 10 may be automatically adjusted after construction of the clothing article in order to achieve a different fit for the wearer of the clothing article. Indeed, the adjustment may be made while the clothing article is being worn. Moreover, the automatic adjustment may also provide other performance changes such as a change in the thermal properties and/or density of the clothing article.

More particularly, the enlarged end view of FIG. 2 demonstrates that the first fabric 10*a* may include a set of threads coupled to one another (e.g., via weaving, knitting, lace making, felting, braiding, plaiting, etc.), wherein a particular thread 12 may operate as a permanent magnet when no electrical current is applied to the thread 12. Similarly, the second fabric 10*b* may include a set of threads coupled to one another, wherein another thread 14 may also operate as a permanent magnet when no electrical current is applied to the thread 14. If the threads 12, 14 have an opposite polarization, positioning the threads 12, 14 adjacent to one another (e.g., at time $t_0$) may create the magnetic bond between the two fabrics 10. Thus, the threads 12, 14 are marked with a pattern fill to indicate the magnetic coupling in the illustrated example.

In order to automatically adjust the relative position between the two fabrics 10, an electrical current may be temporarily applied to a target thread such as, for example, the thread 14 (e.g., at time $t_1$). Due to the electropermanent magnet properties of the thread 14, the electrical current may cause the thread 14 to have no net magnetic field (e.g., no longer operate as a permanent magnet). During such a condition, the illustrated thread 12, which still operates as a permanent magnet, may automatically form a magnetic bond with a nearby thread 16 that operates as a permanent magnet (e.g., provided that the polarizations are different). Thus, the electrical current may initiate a "slide" of the first fabric 10*a* across the second fabric 10*b* (e.g., causing a "snap-in" effect). Once the bond between the threads 12, 16 has been formed, the electrical current may be removed from the thread 14. Removal of the electrical current from the thread 14 may cause the thread 14 to automatically transform back into a permanent magnet and form a magnetic bond with an adjacent thread in the first fabric 10*a*.

The relative position between the two fabrics 10 may be further adjusted by temporarily applying an electrical current to another target thread such as, for example, the thread 16 (e.g., at time $t_2$). Due to the electropermanent magnet properties of the thread 16, the electrical current may cause the thread 16 to have no net magnetic field. During such a condition, the illustrated thread 12, which still operates as a permanent magnet, may automatically form a magnetic bond with a nearby thread 18 that operates as a permanent magnet (e.g., provided that the polarizations are different). Once the bond between the threads 12, 18 has been formed, the electrical current may be removed from the thread 16. Removal of the electrical current from the thread 16 may cause the thread 16 to automatically transform back into a permanent magnet and form a magnetic bond with an adjacent thread in the first fabric 10*a*. The illustrated approach may be readily reversed to slide the fabrics 10 in the opposite direction.

FIG. 3 shows a thread model 20 in which a metal compound 22 is applied, either laterally or longitudinally, to one or more strand substrates 24 (e.g., a relatively flexible textile), wherein the illustrated metal compound 22 has electropermanent magnet properties. More particularly, the metal compound 22 may include an electromagnet 26 (e.g., wire-wound Iron) and a dual material permanent magnet 28 (28*a*, 28*b*). The illustrated dual material permanent magnet 28 includes a magnetically hard material 28*a* (e.g., Neodymium-Iron-Boron/NdFeB, or other alloy having a relatively high intrinsic coercivity) and a magnetically soft material 28*b* (e.g., Iron-Cobalt-Vanadium, or other alloy having a relatively low intrinsic coercivity). Thus, when an electrical current is applied to the electromagnet 26, the magnetization of the soft material 28*b* may change so that the dual material permanent magnet 28 has no net magnetic field. The strand substrates 24 may be selectively coated with various components of the metal compound 22 to achieve the adjustable stitching techniques described herein. Moreover, different fabrics in a particular clothing article may have threads with different metal compounds.

Figure 5A:
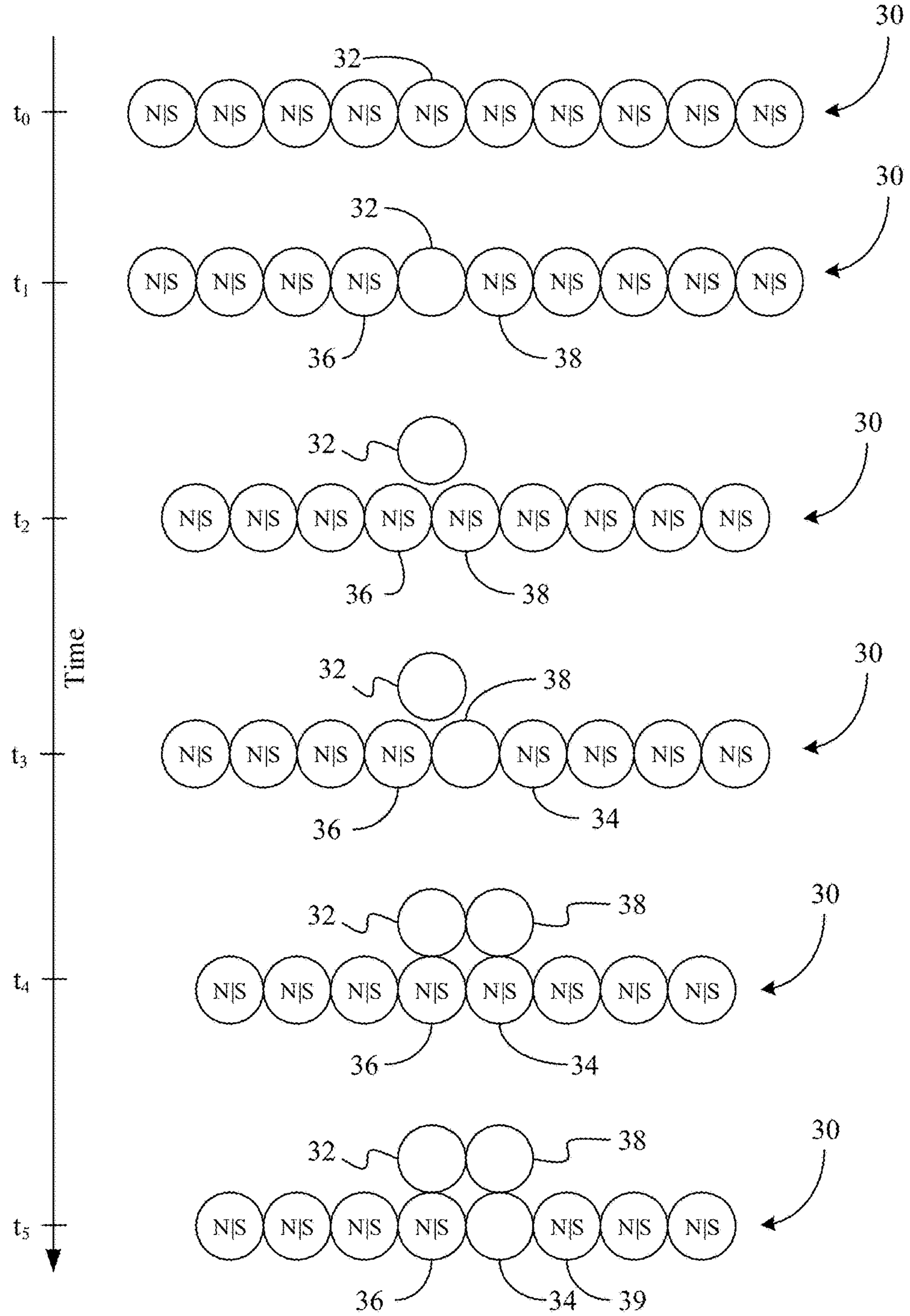
FIGS. 5A-5B are end views of an example of a creation of a fold in a fabric having laterally arranged electropermanent magnet properties according to an embodiment.
Figure 5B:
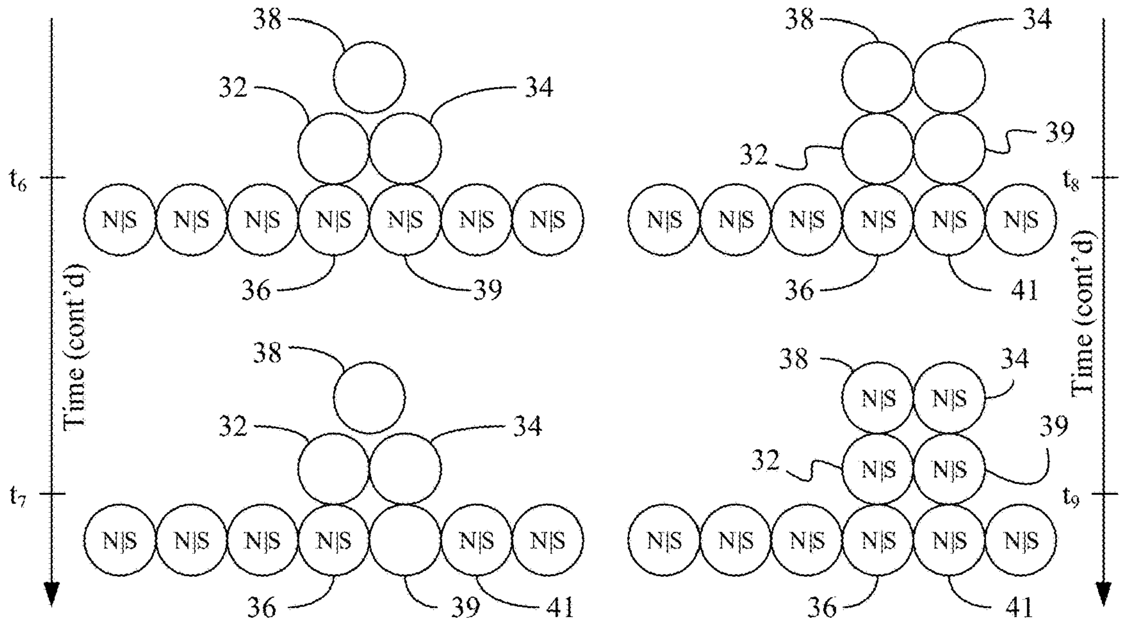

FIGS. 4 and 5A-5B show a fabric 30 having a set of threads coupled to one another, wherein each thread in the set of threads includes a metal compound having laterally arranged electropermanent magnet properties. Thus, the metal compound may be similar to the metal compound 22 (FIG. 3), already discussed. In the illustrated example, the temporary application of an electrical current may generally initiate creation of a fold. More particularly, the electrical current may be applied (e.g., at time $t_1$) to a first target thread 32, wherein the first target thread 32 originally (e.g., at time $t_0$) operates as a permanent magnet (e.g., when no electrical current is applied). The electrical current may cause the first target thread 32 to have no net magnetic field (e.g., no longer operate as a permanent magnet). During such a condition, illustrated threads 36 and 38 may still operate as permanent magnets. Accordingly, the threads 36, 38 may automatically form (e.g., at time $t_2$) a magnetic bond that effectively changes the cut of the fabric 30.

Once the bond between the threads 36, 38 has been formed, the thread 38 may be treated as a second target thread by applying (e.g., at time $t_3$) electrical current to the thread 38. The electrical current may cause the second target thread 38 to have no net magnetic field. Accordingly, threads 36, 34 may automatically form (e.g., at time t4) a magnetic bond with one another. In order to increase the size of the fold, the process may be repeated by applying (e.g., at time $t_5$) electrical current to the thread 34 (e.g., causing it to function as a third target thread and have no net magnetic field). During such a condition, illustrated threads 36, 39 may still operate as permanent magnets. Accordingly, the threads 36, 39 may automatically form (e.g., at time $t_6$) a magnetic bond that increases the size of the fold.

Similarly, the thread 39 may then be treated as a fourth target thread by applying (e.g., at time $t_7$) electrical current to the thread 39. The electrical current may cause the fourth target thread 39 to have no net magnetic field. Accordingly, threads 36, 41 may automatically form (e.g., at time $t_8$) a magnetic bond with one another. Once the appropriate fold size has been achieved, the electrical current may be removed from the target threads 32, 38, 34, 39, wherein removal of the electrical current may automatically transform the target threads 32, 38, 34, 39 back into permanent magnets. The illustrated process may be readily reversed to remove the fold.

Figure 6A:
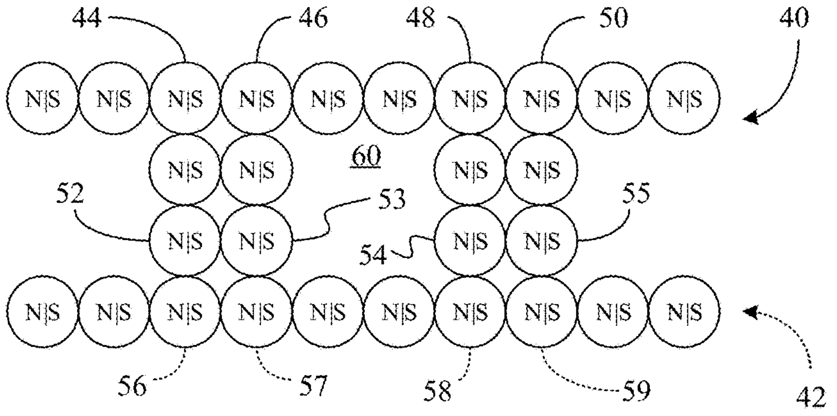
FIGS. 6A-6B are end views of an example of a stacked fold arrangement between a plurality of fabrics having laterally arranged electropermanent magnet properties according to an embodiment.

Turning now to FIG. 6A, an example of a stack fold arrangement between a first fabric 40 (solid) and a second fabric 42 (dashed) is shown. In the illustrated example, folds have been created in the first fabric 40 by using electropermanent magnetic properties and an electrical current to form a magnetic bond between threads 44 and 46, and between threads 48 and 50. A magnetic bond may also be formed between the first fabric 40 and the second fabric 42 by positioning threads 52 and 53 in the first fabric 40 adjacent to threads 56 and 57 in the second fabric 42, and by positioning threads 54 and 55 in the first fabric 40 adjacent to threads 58 and 59 in the second fabric 42. Such an approach may create a void 60 that may be used as mechanical protection and/or shock absorption between the first fabric 40 and the second fabric 42.

Figure 6B:
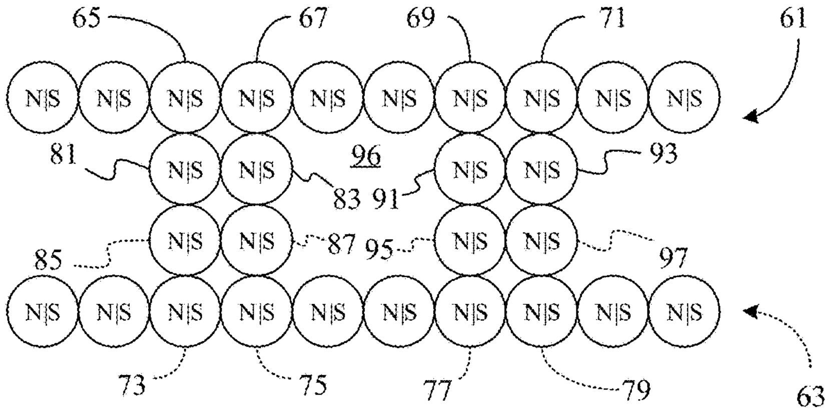

FIG. 6B shows another example of a stacked fold arrangement between a first fabric 61 (solid) and a second fabric 63 (dashed). In the illustrated example, folds have been created in the first fabric 61 by using electropermanent magnet properties and an electrical current to form a magnetic bond between threads 65 and 67, and between threads 69 and 71. Folds may also be created in the second fabric 63 by using electropermanent magnet properties and an electrical current to form a magnetic bond between threads 73 and 75, and between threads 77 and 79. Additionally, a magnetic bond has been formed between the first fabric 61 and the second fabric 63 by positioning threads 81 and 83 adjacent to threads 85 and 87 in the second fabric 63, and by positioning threads 91 and 93 in the first fabric 61 adjacent to threads 95 and 97 in the second fabric 63. Such an approach may create a void 96 that may be used as mechanical protection and/or shock absorption between the first fabric 61 and the second fabric 63.

Turning now to FIG. 7A, a lateral/transverse arrangement is shown in which a thread 98 includes a metal compound having laterally arranged electropermanent magnet properties. In the illustrated example, a magnetically soft material 100 and a magnetically hard material 102 are placed in a transversal section of the thread 98. Accordingly, multiple "slices" of electropermanent magnetic areas may therefore be created along the length of the fabric thread 98. As a result, the illustrated thread 98 has a N-S (North-South) distribution on the left-right sides of the thread 98.

Figure 8:
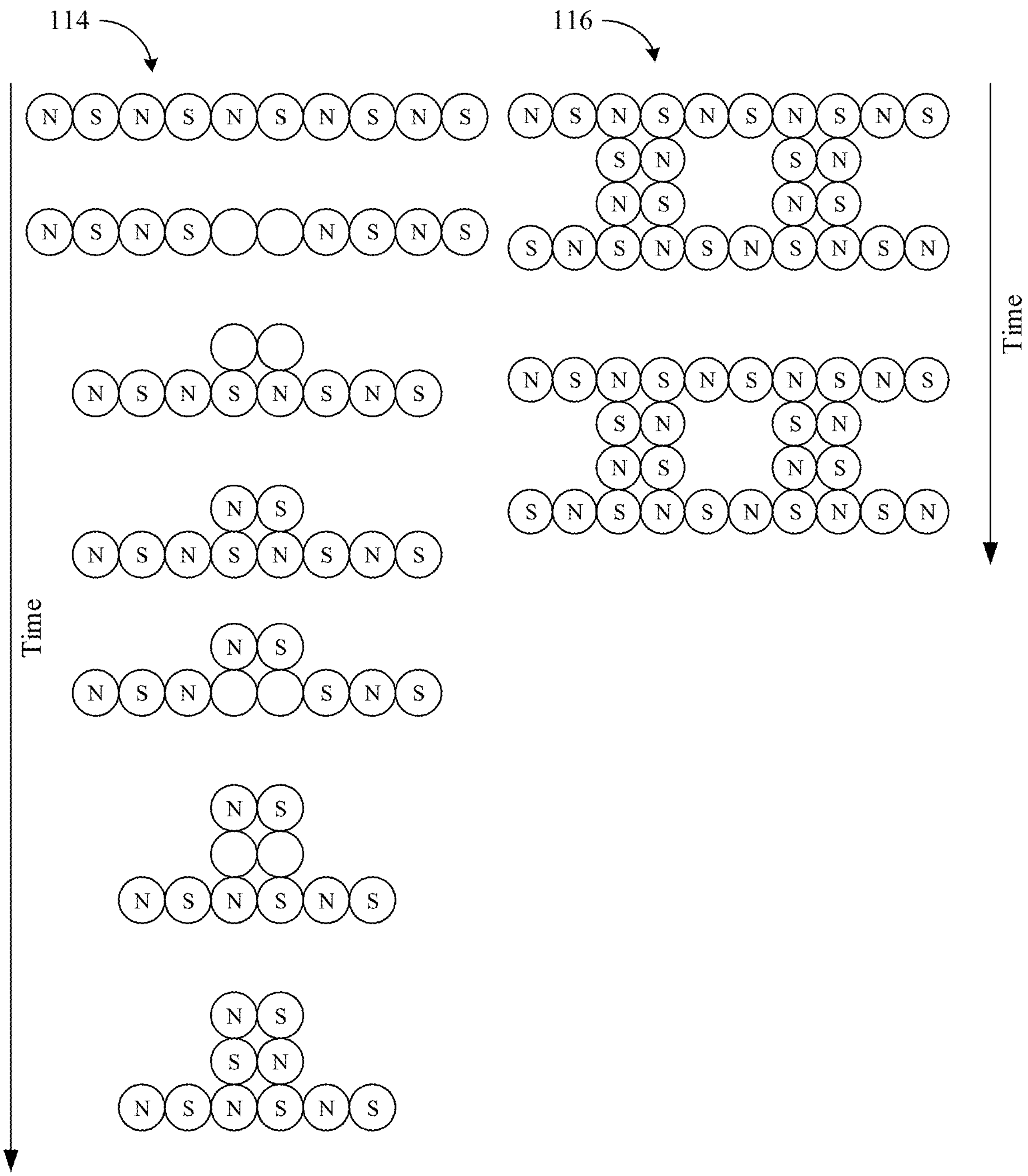
FIG. 8 is an end view of examples of creations of folds and stacked folds having laterally arranged electropermanent magnet properties according to embodiments.

FIG. 7B shows longitudinal arrangements in which threads 104 and 106 generally have a magnetically soft material distributed on the length of the threads 104, 106, from one end to the other. More particularly, the middle of a first thread 104 contains a magnetically hard material 108 and full longitudinal placement of a magnetically soft material 110 in order to create a dual material permanent magnet. The illustrated first thread 104 therefore includes a single N and a single S section for the entire thread 104. In another example, a second thread 106 contains fragmented longitudinal placement of the soft material 110, with multiple placements of the hard material 108 along the second thread 106. The illustrated second thread 106 therefore includes multiple N and S sections for the entire thread. The fragmented longitudinal placement may be a repetition of the full longitudinal placement per thread. In between the repeated sections, there may be flex regions 112 that enable the second thread 106, and also the fabric, to become more flexible. In either example, the result may be a fabric thread with a N-S distribution on the top-bottom sections along the thread full length or partial length (depending on the variant chosen). FIG. 8 shows a fold creation sequence 114 and a stacked fold creation sequence 116 in which the threads have laterally arranged electropermanent magnet properties.

FIG. 9 shows an enlarged plan view of a fabric 62 having a set of threads 64 (64*a*-64*d*) coupled to one another, wherein each thread in the set of threads 64 includes a metal compound having electropermanent magnet properties. In the illustrated example, the fabric 62 also includes a set of transmitters 66 (e.g., digital to analog converters, amplifiers, etc.) coupled to the set of threads 64 and a controller 68 (e.g., integrated circuit/IC chip, processor) coupled to the set of transmitters 66. The controller 68 may select target threads in the fabric 62 and apply electrical current to the selected target threads, wherein the electrical current may initiate creation of folds, slides between the fabric 62 and other fabrics (not shown), and so forth. Additionally, the electrical current may be temporarily applied by the controller 68 (e.g., long enough for other magnetic bonds to form). The illustrated fabric 62 also includes a power source 70 (e.g., battery) to supply power to the controller 68 and/or the transmitters 66. In this regard, the temporary application of the electrical current may enable the physical size and power rating of the power source 70 to be minimized.

In one example, the controller 68 communicates with a mobile platform 72 (e.g., tablet computer, smart phone, mobile Internet device/MID, wearable computer, etc.) that includes logic 74 (e.g., logic instructions, configurable logic and/or fixed-functionality hardware logic) to assist the controller 68 in selecting the target threads. For example, the logic 74 might present a user of the mobile platform 72 with an image of the clothing article as well as various options as to size/fit, temperature specifications, and so forth. In the case of thermal specifications, the mobile platform 72 might measure heart rate, perspiration levels and/or ambient temperature (e.g., using on-platform sensors and/or a network connection) and determine an optimal density of the fabric based on the measurements (e.g., relative to one or more comfort settings associated with the user). Such an approach may be particularly useful in active wear, anti-gravity flight suits (e.g., G suits), and so forth. In another example, the logic 74 may assist the controller 68 in automatically determining the appropriate filtering properties of a surgical mask being worn by medical personnel. The mobile platform 72 may also determine optimal placement and/or size of pockets, which may be useful in, for example, toolbelts, shirts, etc.

The mobile platform 72 may then communicate the selections wirelessly (e.g., via Bluetooth, Wi-Fi, etc.) to the controller 68 in the fabric 62 as well as to other fabrics in the clothing article. Alternatively, the mobile platform 72 may transmit the selections to a single "hub" controller, which may parse and/or relay the selection information to the appropriate fabric controllers. A security layer (e.g., encryption/decryption, authentication) may be superimposed on the wireless communications in order to prevent unauthorized changes in the fabric and/or magnetic stitches.

Although the illustrated view shows only vertical threads 64 for ease of discussion, the threads 64 of the fabric 62 may also be interwoven with a set of horizontal threads having a metal compound with electropermanent magnet properties (e.g., as well as a corresponding set of transmitters). Moreover, the threads having the electropermanent magnet properties may be a subset of all threads in the fabric 62, depending on the circumstances. For example, the electropermanent magnet threads may be selected to be in zones of the fabric 62 that are likely to be used for stitching and/or adjustments (e.g., via sliding or folding).

FIG. 10 shows a method 76 of constructing a clothing article. The method 76 may be implemented using textile manufacturing technology and/or as one or more modules in a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof.

Illustrated processing block 78 provides a first fabric including a first set of threads coupled to one another, wherein each thread in the first set of threads includes a metal compound having electropermanent magnet properties. Block 80 may provide a second fabric including a set of threads coupled to one another, wherein each thread in the second set of threads includes the metal compound having electropermanent magnet properties. Additionally, one or more of the first set of threads may be positioned adjacent to one or more of the second set of threads at block 82. As already noted, positioning the threads adjacent to one another may automatically create a magnetic bond between threads having reverse polarities. In this regard, increasing the number of threads involved in the magnetic bond may generate a force strong enough to hold fabric pieces together while being worn (e.g., during the adjustment).

FIG. 11 shows a method 84 of operating a controller. The method 84 may generally be implemented in a controller such as, for example, the controller 68 (FIG. 9), already discussed. More particularly, the method 84 may be implemented as one or more modules in a set of logic instructions stored in a machine- or computer-readable storage medium such RAM, ROM, PROM, firmware, flash memory, etc., in configurable logic such as, for example, PLAs, FPGAs, CPLDs, in fixed-functionality hardware logic using circuit technology such as, for example, ASIC, CMOS or TTL technology, or any combination thereof.

Illustrated processing block 86 may determine whether a relative shift between fabrics in a clothing article is to be conducted. Block 86 may including decrypting, authenticating, parsing and/or analyzing one or more communications from a mobile platform such as, for example, the mobile platform 72 (FIG. 9). If it is determined that a relative shift is to be conducted, illustrated block 88 selects one or more target threads from a first set of threads in a first fabric and a second set of threads in a second fabric. An electrical current may be temporarily applied to the target threads at block 90 (e.g., via a first set of transmitters and a second set of transmitters, respectively), wherein the electrical current initiates the relative shift. Additionally, a determination may be made at block 92 as to whether a fold of a fabric in the clothing article is to be conducted (e.g., in order to change the cut). Block 92 may also include decrypting, authenticating, parsing and/or analyzing one or more communications from a mobile platform such as, for example, the mobile platform 72 (FIG. 9). If it is determined that a fold is to be conducted, illustrated block 94 selects one or more target threads in a fabric, wherein an electrical current may be temporarily applied to the target threads at block 90 (e.g., via a set of transmitters), wherein the electrical current initiates the fold. The method 84 may be repeated iteratively to obtain a particular size and/or cut for the clothing article.

ADDITIONAL NOTES AND EXAMPLES

Example 1 may include a clothing article comprising a first fabric including a first set of threads coupled to one another, wherein each thread in the first set of threads includes a metal compound having electropermanent magnet properties, and a second fabric coupled to the first fabric, the second fabric including a second set of threads coupled to one another, wherein each thread in the second set of threads includes the metal compound having electropermanent magnet properties.

Example 2 may include the clothing article of Example 1, wherein the metal compound includes an electromagnet, and a dual material permanent magnet.

Example 3 may include the clothing article of any one of Examples 1 or 2, further including a first set of transmitters coupled to the first set of threads, a second set of transmitters coupled to the second set of threads, and one or more controllers coupled to the first set of transmitters and the second set of transmitters, the one or more controllers to apply electrical current to one or more target threads in one or more of the first set of threads or the second set of threads via one or more of the first set of transmitters or the second set of transmitters, respectively.

Example 4 may include the clothing article of Example 3, wherein the electrical current is to initiate creation of a fold among the one or more target threads.

Example 5 may include the clothing article of Example 3, wherein the electrical current is to initiate a slide of the first fabric across the second fabric.

Example 6 may include the clothing article of Example 3, wherein the one or more controllers are to temporarily apply the electrical current to the one or more target threads.

Example 7 may include the clothing article of Example 1, further including a power source.

Example 8 may include a fabric comprising a set of threads coupled to one another, wherein each thread in the set of threads includes a metal compound having electropermanent magnet properties.

Example 9 may include the fabric of Example 8, wherein the metal compound includes an electromagnet, and a dual material permanent magnet.

Example 10 may include the fabric of any one of Examples 8 or 9, further including a set of transmitters coupled to the set of threads, and a controller coupled to the set of transmitters, the controller to apply electrical current to one or more target threads in the set of threads via the set of transmitters.

Example 11 may include the fabric of Example 10, wherein the electrical current is to initiate creation of a fold among the one or more target threads.

Example 12 may include a method of operating a controller, comprising applying an electrical current to one or more target threads in one or more of a first set of threads or a second set of threads via one or more of a first set of transmitters or a second set of transmitters, respectively, wherein the first set of threads is part of a first fabric and the second set of threads is part of a second fabric, and wherein each thread in the first set of threads and the second set of threads includes a metal compound having electropermanent magnet properties.

Example 13 may include the method of Example 12, wherein the electrical current initiates creation of a fold among the one or more target threads.

Example 14 may include the method of Example 12, wherein the electrical current initiates a slide of the first fabric across the second fabric.

Example 15 may include the method of any one of Examples 12 to 14, wherein the electrical current is temporarily applied to the one or more target threads.

Example 16 may include at least one non-transitory computer readable storage medium comprising a set of instructions, which when executed by a controller, cause the controller to apply electrical current to one or more target threads in one or more of a first set of threads or a second set of threads via one or more of a first set of transmitters or a second set of transmitters, respectively, wherein the first set of threads is part of a first fabric and the second set of threads is part of a second fabric, and wherein each thread in the first set of threads and the second set of threads includes a metal compound having electropermanent magnet properties.

Example 17 may include the at least one non-transitory computer readable storage medium of Example 16, wherein the electrical current is to initiate creation of a fold among the one or more target threads.

Example 18 may include the at least one non-transitory computer readable storage medium of Example 16, wherein the electrical current is to initiate a slide of the first fabric across the second fabric.

Example 19 may include the at least one non-transitory computer readable storage medium of any one of Examples 16 to 18, wherein the electrical current is to be temporarily applied to the one or more target threads.

Example 20 may include a method of constructing a clothing article, comprising providing a first fabric including a first set of threads coupled to one another, wherein each thread in the first set of threads includes a metal compound having electropermanent magnet properties, providing a second fabric including a second set of threads coupled to one another, wherein each thread in the second set of threads includes the metal compound having electropermanent magnet properties, and positioning one or more of the first set of threads adjacent to one or more of the second set of threads.

Example 21 may include the method of Example 20, wherein the metal compound includes an electromagnet, and a dual material permanent magnet.

Example 22 may include the method of any one of Examples 20 or 21, further including applying electrical current to one or more target threads in one or more of the first set of threads or the second set of threads via one or more of a first set of transmitters or a second set of transmitters, respectively.

Example 23 may include the method of Example 22, wherein the electrical current initiates creation of a fold among the one or more target threads.

Example 24 may include the method of Example 22, wherein the electrical current initiates a slide of the first fabric across the second fabric.

Example 25 may include the method of Example 22, wherein the electrical current is temporarily applied to the one or more target threads.

Example 26 may include a controller to construct clothing articles, comprising means for providing a first fabric including a first set of threads coupled to one another, wherein each thread in the first set of threads includes a metal compound having electropermanent magnet properties, means for providing a second fabric including a second set of threads coupled to one another, wherein each thread in the second set of threads includes the metal compound having electropermanent magnet properties, means for positioning one or more of the first set of threads adjacent to one or more of the second set of threads.

Example 27 may include the controller of Example 26, wherein the metal compound is to include an electromagnet, and a dual material permanent magnet.

Example 28 may include the controller of any one of Examples 26 or 27, further including means for applying electrical current to one or more target threads in one or more of the first set of threads or the second set of threads via one or more of a first set of transmitters or a second set of transmitters, respectively.

Example 29 may include the controller of Example 28, wherein the electrical current is to initiate creation of a fold among the one or more target threads.

Example 30 may include the controller of Example 28, wherein the electrical current is to initiate a slide of the first fabric across the second fabric.

Example 31 may include the controller of Example 28, wherein the electrical current is to be temporarily applied to the one or more target threads.

Thus, techniques may provide for dynamically adjusting the bond lines between fabrics and folding excess fabric in order to modify articles of clothing both in size and tailor cut. The programmable bond lines may be located anywhere on the fabric, while enabling clean clothing cuts to be automatically obtained without the expense or time of manual tailoring. Moreover, the amount of time involved in bonding fabric pieces together may be small enough to be considered instantaneous from the perspective of the wearer.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" may mean any combination of the listed terms. For example, the phrases "one or more of A, B or C" may mean A, B, C; A and B; A and C; B and C; or A, B and C.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A clothing article comprising:

a first fabric including a first set of threads coupled to one another, wherein each thread in the first set of threads includes a metal compound having electropermanent magnet properties, wherein the metal compound includes an electromagnet and a dual material permanent magnet; and a second fabric coupled to the first fabric, the second fabric including a second set of threads coupled to one another, wherein each thread in the second set of threads includes the metal compound having electropermanent magnet properties.

2. The clothing article of claim 1, further including:

a first set of transmitters coupled to the first set of threads;

a second set of transmitters coupled to the second set of threads; and one or more controllers coupled to the first set of transmitters and the second set of transmitters, the one or more controllers to apply electrical current to one or more target threads in one or more of the first set of threads or the second set of threads via one or more of the first set of transmitters or the second set of transmitters, respectively.

3. The clothing article of claim 2, wherein the electrical current is to initiate creation of a fold among the one or more target threads.

4. The clothing article of claim 2, wherein the electrical current is to initiate a slide of the first fabric across the second fabric.

5. The clothing article of claim 2, wherein the one or more controllers are to temporarily apply the electrical current to the one or more target threads.

6. The clothing article of claim 1, further including a power source.

7. A fabric comprising:

a set of threads coupled to one another, wherein each thread in the set of threads includes a metal compound having electropermanent magnet properties, wherein the metal compound includes an electromagnet and a dual material permanent magnet.

8. The fabric of claim 7, further including:

a set of transmitters coupled to the set of threads; and a controller coupled to the set of transmitters, the controller to apply electrical current to one or more target threads in the set of threads via the set of transmitters.

9. The fabric of claim 8, wherein the electrical current is to initiate creation of a fold among the one or more target threads.

10. A method of constructing a clothing article, comprising:

providing a first fabric including a first set of threads coupled to one another, wherein each thread in the first set of threads includes a metal compound having electropermanent magnet properties, wherein the metal compound includes an electromagnet and a dual material permanent magnet;

providing a second fabric including a second set of threads coupled to one another, wherein each thread in the second set of threads includes the metal compound having electropermanent magnet properties;

positioning one or more of the first set of threads adjacent to one or more of the second set of threads.

11. The method of claim 10, further including:

applying electrical current to one or more target threads in one or more of the first set of threads or the second set of threads via one or more of a first set of transmitters or a second set of transmitters, respectively.

12. The method of claim 11, wherein the electrical current initiates creation of a fold among the one or more target threads.

13. The method of claim 11, wherein the electrical current initiates a slide of the first fabric across the second fabric.

14. The method of claim 11, wherein the electrical current is temporarily applied to the one or more target thread.

* * * * *